United States Patent [19]

Sakashita et al.

[11] Patent Number: 5,439,830
[45] Date of Patent: Aug. 8, 1995

[54] METHOD OF PERFORMING AT IMMUNOASSAY USING PHOTOTHERMAL DEFLECTION SPECTROSCOPY

[75] Inventors: Hajime Sakashita, Setagaya; Hiroshi Kishioka, Yokkaichi; Shohei Konishi, Setagaya; Tsuguo Swada, Arakawa; Takahiko Kitamori, Matsudo, all of Japan

[73] Assignee: Kyowa Hakko Kogyo Co., Ltd., Tokyo, Japan

[21] Appl. No.: 138,069

[22] Filed: Oct. 20, 1993

[30] Foreign Application Priority Data

Oct. 20, 1992 [JP] Japan .................................. 4-281330

[51] Int. Cl.⁶ .......................................... G01N 33/546
[52] U.S. Cl. ..................................... 436/534; 436/523; 436/525; 436/527; 436/528; 436/531; 436/537; 436/533; 435/962
[58] Field of Search ............... 436/531, 518, 523, 525, 436/533, 527, 528, 534, 537; 250/574; 356/432, 436; 372/53; 435/7.91, 7.92, 7.94, 962

[56] References Cited

U.S. PATENT DOCUMENTS

| | | | |
|---|---|---|---|
| 4,544,274 | 10/1985 | Cremers et al. | 356/436 |
| 4,790,664 | 12/1988 | Saito et al. | 356/432 |
| 4,867,840 | 9/1989 | Roxlo et al. | 156/643 |
| 5,268,746 | 12/1993 | Masetti et al. | 356/432 |

OTHER PUBLICATIONS

T. Masujima et al, "Biological Component Microanalysis By Laser Photoacoustic Imaging Immunoassay," Chem. Pharm. Bull, 37(4) 1123–1125 (1989).

M. Harada et al., "Effects of Probe Beam Offset on Quantitative Measurement in Photothermal Beam Deflection Spectroscopy" in Anal. Chem. vol. 65 (1993 Aug. 1) pp. 2181–2183.

S. Matsuzawa et al, "Quantitation of IgE and ... CEA by optical beam deflection (OBD) measurement of dot immunobinding assay patterns visualized by an ELISA technique" in J. of Immunol. Methods vol. 161 No. 1 (5 May 1993) pp. 59–65.

C. Tu et al., "Ultrasensitive Heterogeneous Immunoassay Using Photothermal Deflection Spectroscopy" in Anal. Chem. vol. 65 (15 Dec. 1993) pp. 3631–3635.

T. Masujima, et al., Photoacoustic and Photothermal phenomena, 58, 558 (1988).

Obata et al., Analytical Sciences, vol. 7 Supp. (1991) 1387–88.

Wu et al., Analytical Chemistry, vol. 63, No. 3 (1991) 217–219.

Nolan et al., IEEE Circuits and Devices Magazine, vol. 2, No. 1 (1986) 54–56.

Kitamori et al., Anal. Chem., vol. 63, No. 3 (1991) 217–19.

*Primary Examiner*—Carol A. Spiegel
*Attorney, Agent, or Firm*—Fitzpatrick, Cella, Harper & Scinto

[57] ABSTRACT

In an immunoassay for determining the amount of a target substance in a sample using photothermal deflection spectroscopy to determine the amount of bound label, a sandwich procedure is used which comprises reacting the target substance with two antibodies or antigens, one labelled with a compound having photothermal deflection activity, and the other immobilized on a carrier capable of amplifying that photothermal conversion activity of the label.

3 Claims, 1 Drawing Sheet

METHOD OF PERFORMING AT IMMUNOASSAY USING PHOTOTHERMAL DEFLECTION SPECTROSCOPY

FIELD OF THE INVENTION

The present invention relates to a method of performing an immunoassay wherein photothermal deflection spectroscopy is used as the measurement technique. More particularly, it related to a method for determining the amount of an antigen or an antibody in a sample using photothermal deflection spectroscopy.

BACKGROUND OF THE INVENTION

Photothermal deflection spectroscopy is a new measurement technique and has been disclosed, for example, in Analytical Chemistry, 63, 217 (1991).

The principle of photothermal deflection spectroscopy is as follows:

A sample is irradiated with an excitation beam of specified wavelength. As a result, compounds having photothermal conversion activity corresponding to that wavelength generate heat and the quantity of the heat produced is measured by the deflection of a probe beam which passes through the sample. The amount of the target compound present in the sample is determined from the amount of heat produced.

The application of this technique to immunoassays using a compound having photothermal conversion activity as a marker is the same kind of marker as the radioisotope used in radioimmunoassays, is known from Analytical Science, 7, 1387 (1991). However, immunoassays using a carrier capable of amplifying the photothermal deflection effect are not known.

In general, immunoassays are classified as either heterogenous or homogeneous. In a heterogenous assay, after the substance to be assayed is reacted with an antigen or an antibody having a marker bound thereto, the bound and the free markers are separated (B/F separation), and washed prior to measurement. Homogeneous assays are carried out without any B/F separation, but have so far not yet been used in immunoassays using photothermal deflection spectroscopy as the measurement technique.

Homogeneous immunoassays have the advantage that the measurement can readily be carried out using simple procedures after only a short period of time. However, in the homogeneous assay the sample will contain not only the reacted marker (i.e. bound marker) but also unreacted marker (i.e. unbound marker). The detected signals from the sample will therefore include a signal (S), derived from the bound marker, and a signal (N), derived from the unbound marker. The signal-to-noise (S/N) ratio in a homogeneous assay is therefore low. For this reason, homogeneous immunoassays are of low precision, and there is a great demand for improvement.

SUMMARY OF INVENTION

In accordance with the present invention, the present inventors have developed an immunoassay which can attain a high degree of precision even in a homogeneous assay. This is achieved using an antibody or antigen immobilised onto a compound capable of amplifying the photothermal deflection effect obtained when the immunoconjugate, formed during the assay, is irradiated.

As a result the S/N ratio obtained using photothermal deflection spectroscopy is much improved.

Accordingly, the present invention provides an immunoassay for determining the amount of substance to be assayed in a sample, which comprises treating the sample with an antibody or antigen having a specific binding capacity for the target substance and capable of forming an immunoconjugate therewith, said antibody or antigen being linked to a compound which, when irradiated with an excitation beam of a given wavelength, gives rise to a photothermal conversion effect, and determining the amount of immunoconjugate formed between the target substance and the antibody or antigen by photothermal deflection spectroscopy, wherein the said immunoconjugate is formed by treating the sample with two different antibodies or antigens, both having a specific binding capacity for the target substance and being capable of forming therewith an immunoconjugate consisting of the target substance and both antibodies or antigens, the one antibody or antigen being linked to the compound providing said photothermal conversion effect and the other being linked to a carrier substance that amplifies the photothermal activity of said compound when the immunoconjugate is irradiated with the excitation beam during determination of the immunoconjugate by photothermal deflection spectroscopy.

In this method the S/N ratio is improved since only signals from the bound marker are amplified.

The method of the invention is applicable to both heterogenous assays with a simplified B/F separation or to homogeneous assays with no B/F separation.

DETAILED DESCRIPTION OF THE INVENTION

Figure 1:
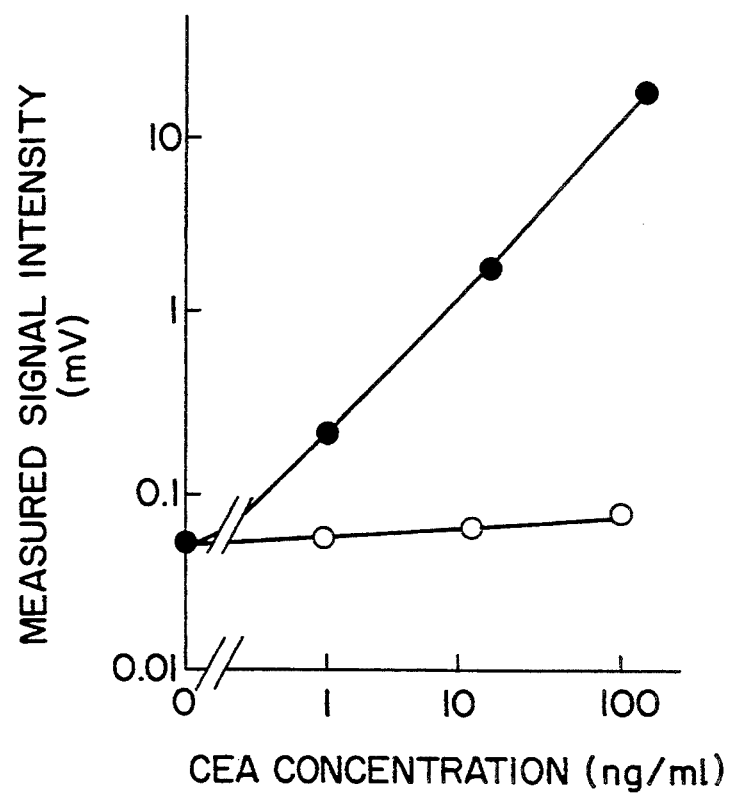
FIG. 1 is a graph showing the calibration curves for carcinoembryonic antigen (CEA) immunoassay in which the data obtained by the method of the present invention and using a second antigen coupled to a carrier capable of amplifying the photothermal activity of a photothermally active compound attached to a first antigen are represented by closed circles, while the data obtained using the first antigen alone (control) are represented by open circles.

In the known method of determining the amount of a substance to be assayed in a sample by a photothermal deflection immunoassay, the amount of the substance to be assayed is determined by an antigen-antibody reaction between the target substance and a corresponding antibody or antigen coupled to a compound having photothermal conversion activity and which acts as a marker. Heat generated from the bound marker, when it is excited by the excitation beam, is measured via the deflection of a light beam passing through the sample and the amount of the target substance in the sample is determined from the measured quantity of the heat.

In the method of the present invention, two antigen-antibody reactions are employed, i.e., the sandwich method. In one step, usually the first step, the reaction is between the substance to be assayed and an immobilized antibody or antigen; in the other reaction, the reaction is between the target substance, normally in the form of immune complex already formed by the first antigen-antibody reaction, and a second antibody or antigen coupled to a marker compound which provides a photothermal conversion effect when irradiated. The immobilized antibody or antigen used in the first step is bound to a carrier capable of amplifying photothermal conversion activity of the marker on the second antibody or antigen, thereby to increasing the photothermal deflection effect when the samples containing the immunoconjugate is irradiated with the excitation beam.

Examples of target (antigen or antibody) substances to be assayed are proteins such as carcinoembryonic antigen (CEA), immunoglobulins (IgG, IgA, IgM, IgD, IgE), complements (C3, C4, C5, C1q), C-reactive protein (CRP), $\alpha_1$-antitrypsin, $\alpha_1$-microglobulin, $\beta_1$-microglobulin, haptoglobulin, transferrin, ceruloplasmin, ferritin, albumin, haemoglobin $A_1$, haemoglobin $A_{1c}$, myoglobin, myosin, dupan-2, $\alpha$-fetoprotein (AFP), prostate-derived acid phosphatase (PAP), tissue polypeptide antigen (TPA), nerve-specific enolase (NSE), apolipoprotein $A_1$, apolipoprotein E, rheumatoid factors, anti-streptolysin O (ASO), fibrinogen, fibrin degradation products (FDP), fibrin degradation product D fraction (FDP-D), fibrin degradation product D—D fraction (FDP-D Dimer), fibrin degradation product E fraction (FDP-E), antithrombin-III (AT-III), fibrinogen and plasminogen; enzymes such as elastase and creatine kinase of myocardium type (CK-MB); hormones such as insulin, thyroid-stimulating hormone (TSH), 3,5,3'-triiodothyronine ($T_3$), thyroxine ($T_4$), adrenocorticotropic hormone (ACTH), growth hormone (GH) and luteinizing hormone (LH); antigens and antibodies associated with or against etiogenic viruses of various infectious diseases, such as hepatitis B virus associated antibody, hepatitis B virus associated antigen, hepatitis C virus associated antibody, adult T cell leukaemia virus (HTLV) associated antibody, acquired immune deficiency syndrome (AIDS) virus associated antibody, Chlamydia antibody, syphilis antibody and toxoplasma antibody.

Where the target compound to be assayed is an antigen the corresponding antibody may be prepared by the usual methods, either as a polyclonal antibody or as a monoclonal antibody (see for example "Monoclonal Antibody Experimental Manual", edited by Sakuji Tomiyama et al., Kodan-sha Scientific, 1987; and New Lectures on Biochemical Experiments, vol 12, "Molecular Immunology III, Antigens, Antibodies and Complements", edited by the Biochemical Society of Japan, Tokyo Kagaku Dohjin-sha, 1992).

Where the target compound is an antibody, the corresponding antigen can be prepared by genetic manipulation and replication of the antibody-binding sites (epitopes) of the natural antigen or the complete antigen. For example, in cases where the target compound is an antibody against an etiogenic virus of an infectious disease, various marker proteins derived from the virus can be used as the antigen for the target antibody.

As the carrier capable of amplifying photothermal conversion activity of the label on the labelled antibody or antigen a substance will be used that cannot absorb light at around the wavelength of the excitation beam that is used to excite the label during the subsequent photothermal deflection spectroscopy. Examples of suitable carriers are organic polymer particles or latices, or fine particles of an inorganic material. Typical examples of suitable organic polymer latices or particles are polystyrene, carboxylated polystyrene, polyvinyltoluene, styrene-divinylbenzene copolymer, styrene-butadiene copolymer, carboxylated styrene-butadiene copolymer, acrylic ester copolymer and methacrylic ester copolymer. Typical inorganic materials are particles of finely divided glass or kaolin. Typically the carrier particles will have a mean diameter in the range of from 1 to 500 $\mu$m, preferably from 10 to 50 $\mu$m.

The appropriate antibody or antigen can be immobilized onto the carrier by a variety of different methods. Suitable chemical binding methods include, for example, the diazo method, the peptide method, the alkyl method, or by cross-linking with a cross-linking reagent such as carbodiimide, N-succinimidyl-2-pyridylthio-3-propionic acid (SPDP), or cyanogen chloride. Alternatively, the antigen or antibody can be immobilized onto the carrier by physical adsorption hydrophobic bonding, for example as described in new Lectures on Biochemical Experiments, vol 1, "Proteins IV, Correlation between Structure and Function", edited by the Biochemical Society of Japan, Tokyo Kagaku Dohjin-sha, 1991; or in "Immobilized Enzymes", edited by Ichiro Chihata, Kohdan-sha Scientific. 1975.

As the compound or label providing the photothermal conversion effect, a variety of chemical compounds exhibiting a specific absorption of light in the wavelength range of from 200 to 1000 nm may be used. Typical examples are dyes such as azo dyes, quinone dyes, polyene dyes, phenothiadione dyes, indigo dyes, triphenylmethane dyes, polymethine dyes, acridine dyes, phthalocyanine dyes and squaric acid dyes. Other suitable photothermic labels include metals such as colloidal gold, inorganic complexes such as iron-oxine complexes and heme; metal-containing proteins such as peroxidase, haemoglobin, cytochrome and chlorophyll, and chromoproteins such as phycocyanin.

The compound having photothermal conversion activity, i.e., the label, can be bound directly or indirectly to the appropriate antibody or antigen. Suitable direct binding methods are those already described with reference to the immobilized antibody or antigen. Where the compound having photothermal conversion activity is bound indirectly to the antibody or antigen, this can be via an intermediate carrier, onto which the antibody or antigen is immobilized in the manner described, but using as a carrier a material which has neither photothermal conversion activity, nor amplification activity for the photothermal deflection effect. A suitable inert carrier in this respect is provided by polystyrene latex beads having a mean diameter of 0.5 $\mu$m or less.

The first of the two antigen-antibody reactions involved in the method of the present invention may be effected under conventional conditions for antigen-antibody reactions; for example, the immobilized antibody or antigen is reacted with the target substance in the sample in the presence of a buffer, e.g. a neutral, weakly acidic or weakly basic phosphate buffer, or a tris-hydrochloric acid buffer, etc. The reaction is carried out at 4° C. to 40° C. over a period of from 30 seconds to 24 hours. The second, labelled antibody or antigen is then added to the reaction solution containing the immunoconjugate formed by the first antigen-antibody reaction. The second antigen-antibody reaction between the labelled antibody or antigen and the previously formed immunoconjugate is performed at 4° C. to 40° C. over a period of from 30 seconds to 72 hours. At that time, various additives can be added to the reaction system, such as reaction accelerators and stabilizers (e.g. albumin). Any additives are usable, so long as they have no deleterious effect on the present invention, such as inactivation of the substances to be assayed, inhibition of the antigen-antibody reactions, or inhibition of the measurement to be made by photothermal deflection spectroscopy.

Instead of the two step reaction described, it may be possible that both the immobilized antibody or antigen and the labelled antibody or antigen are reacted with the target substance at the same time. The experimental conditions for such a one step reaction will be the same as the experimental conditions used in the two step reaction. It may also be possible to carry out the two steps in reverse order.

After the second step antigen-antibody reaction, the immunoconjugate comprising the target substance sandwiched between the immobilized antibody or antigen and the labelled antibody or antigen can be determined by conventional photothermal deflection spectroscopy with or without separation from the sample. Preferably, the photothermal deflection spectroscopy is as described below.

After completion of the second antigen-antibody reaction, the reaction solution is put in a cell made of synthetic quartz, ordinary glass, Pyrex TM, polystyrene or polymethacrylate, and the cell placed in an apparatus for photo thermal deflection spectroscopy. Alternatively, the immunoassay procedure can itself be effected in such a cell already placed in the measurement apparatus. The cell containing the reaction solution is then irradiated with an excitation beam from the light source of the photothermal deflection spectroscopy apparatus. The excitation beam may be applied to the reaction solution at any angle. Irradiation of the bound label by the excitation beam generates heat because of the photothermal conversion activity of the label and since the immunoconjugate carrying the bound label also comprises the carrier capable of amplifying the photothermal conversion activity of the label, the immobilized antibody or antigen increases the heat derived from the antibody or antigen labelled with the compound providing that photothermal conversion activity. Then, by measuring the deflection of the probe beam passing through the sample, the heat generated by the exothermal reaction can be measured thereby to determine the amount of bound marker. Moreover, since the heat generated in the sample is mostly derived from the second antibody or antigen which is bound to the target substance along with the immobilized antibody or antigen which amplifies the photothermal conversion activity, the determined amount of bound marker substantially corresponds to the amount of the target substance in the sample. In other words, the quantitative determination of the target substance can be carried out in a homogeneous system, and using photothermal deflection spectroscopy as the measurement technique.

The light source used in the photothermal deflection spectroscopy may be any suitable source which emits a light beam having a specified wavelength. Preferably a laser source is used. Typical examples of suitable laser sources are helium-neon lasers, excimer lasers, argon lasers, carbon dioxide gas lasers, ruby lasers, Nd-YAG lasers, semiconductor lasers and dye lasers. In cases where an argon laser is to be used as the light source, the preferred labels giving photothermal conversion activity are azo dyes such as Sunset Yellow; inorganic complexes such as iron-oxine complex and heme; and metals such as colloidal gold. In cases where a semiconductor laser is used as the light source, it is preferred to use a dye, e.g. a cyanine-type dye, a squalinic-type dye, or a phthalocyanine-type dye, as the label. The wavelength of the excitation light beam can be anything from the ultraviolet region of the spectrum through the visible region to the near-infrared region, depending on the absorption characteristics of the label. Preferred are wavelengths in the range of from 200 to 1000 nm.

The invention is illustrated by the following example and the reference example, but which are not to be construed as limiting the scope of the invention.

EXAMPLE (1) Preparation of Immobilized Mouse Anti-CEA Antibody

A buffered polystyrene latex (1%) was prepared by adding a 10% (w/V) polystyrene latex (particle diameter 10 μM) (The Dow Chemical Co.) to a 0.1M phosphate buffer (pH 7). 1 mg of mouse anti-carcinoembryonic antigen (CEA) antibody (Takara Shuzo Co Ltd) was added to 1 ml of the buffered latex and the mixture stirred at 37° C. for about 2 hours. The supernatant was removed by centrifuging at 5000 rpm for 20 minutes, and the resulting immobilized CEA antibody was re-dispersed in a 0.1M phosphate buffer (pH 7) containing 0.5% bovine serum albumin.

(2) Preparation of Second Antibody 1 ml of a standard iron solution (Wako Pure Chemical Industries Ltd; 1000 ppm) was mixed with 2 ml of 1M acetate buffer (pH 4) containing 0.85% oxine, and the pH of the mixture was adjusted to 4 by the addition of a 1M acetate buffer. 1 ml of a 1% polystyrene latex, prepared by adding a 10% (w/v) polystyrene latex (particle mean diameter 0.07 μm) (The Dow Chemical Co.) to water, was added to the buffered iron-oxine solution and the mixture stirred at room temperature for 2 hours. The iron-oxine bound latex particles were recovered by filtration and drying. The particles were resuspended in a 0.1M phosphate buffer (pH 7) to provide a latex containing 1% iron-oxine bound latex particles. 1 ml of mouse-derived anti-CEA antibody (Seikagaku Kogyo, 1 mg/ml) was added to 1 ml of that buffered iron-oxine latex and the mixture was stirred at 37° C. for about 2 hours. The supernarant was removed by centrifuging at 12,000 rpm for 50 minutes and the precipitate re-suspended in a 0.1M phosphate buffer (pH 7). The suspension was stirred, centrifuged again at 12,000 rpm for 50 minutes to remove the supernatant liquid. The resulting second antibody was re-dispersed in a 0.1M phosphate buffer (pH 7) containing 0.5% bovine serum albumin.

(3) Determination of CEA 0.05 mg of the immobilized mouse anti-CEA antibody particles (1) was reacted with CEA (1 ng/ml or 100 ng/ml) in a phosphate buffer at 37° C. for 10 minutes. The reaction solution was then poured in a cell, which was then placed in an apparatus for photothermal deflection spectroscopy. The cell was irradiated with an excitation light beam from argon ion laser (having a wavelength of 488 nm) modulated by a mechanical light chopper at a frequency of 320 Hz, and the resulting deflection of the probe light beam was measured. The measured signal intensities are shown in Table 1, and the calibration curve for CEA is shown in FIG. 1.

TABLE 1

| CEA conc. | Signal Intensities (mV) | |
|---|---|---|
| (ng/ml) | Example | Reference |
| 0 | 0.05 | 0.05 |
| 1 | 0.25 | 0.06 |
| 10 | 2.13 | 0.08 |

TABLE 1-continued

| CEA conc. | Signal Intensities (mV) | |
| --- | --- | --- |
| (ng/ml) | Example | Reference |
| 100 | 20.59 | 0.10 |

As can be seen from Table 1 and FIG. 1, the method of this example, using a second CEA-Antibody immobilized onto a carrier (polystyrene latex particles having a mean diameter of 10 μm) capable of amplifying photothermal deflection in a sandwich immunoassay using thermal deflection spectroscopy gave a good calibration curve, even in a homogeneous assay.

Further, for the purpose of measuring the S/N ratio, the immunoassay was repeated and the reaction solution was centrifuged at 5000 rpm for 20 minutes to separate the solid phase (containing bound markers) and the liquid phase (containing unbound markers). The liquid phase and the solid phase, re-suspended in a buffer, were poured in separate cells which were then subjected to the measurement of signal intensities by photothermal deflection spectroscopy as before. The results are shown in Table 2.

TABLE 2

| | Signal Intensities (mV) | |
| --- | --- | --- |
| | Example | Reference |
| Bound (solid phase) | 0.20 | 0.01 |
| Unbound (liquid phase) | 0.05 | 0.05 |
| S/N | 4.00 | 0.20 |

REFERENCE EXAMPLE

The amounts of CEA (1 ng/ml, 10 ng/ml and 100 ng/ml) in a sample were measured in the same manner as described in the preceding Example, except that free mouse-derived anti-CEA antibody (0.05 mg) was used as the first antibody. The measured signal intensities are shown in Table 1, and the calibration curve for CEA is shown in FIG. 1.

As can be seen from Table 1 and FIG. 1, an anti-CEA antibody immobilized onto a carrier capable of amplifying photothermal deflection effect gave a better calibration curve, as compared with Reference Example where no such carrier was used.

Further, for the purpose of measuring the S/N ratio, the signal intensities of the solid phase (containing bound markers) and the liquid phase (containing unbound markers) were measured in the same manner as described in the preceding Example. The results are shown in Table 2.

As can be seen from Table 2, an anti-CEA antibody immobilized onto a carrier capable of amplifying photothermal activity of the label gave a significantly improved S/N ratio, as compared with Reference Example where no such carrier was used.

What is claimed is:

1. An immunoassay method for determining the amount of a target substance in a test sample, comprising:
   (1) reacting the sample with a first immobilized antibody or antigen having a specific binding capacity for the target substance to form an immune complex wherein said immobilized antibody or antigen is linked to a carrier substance having a mean diameter of from 1 to 500 μm selected from the group consisting of polystyrene, carboxylated polystyrene, polyvinyltoluene, styrene-divinylbenzene copolymer, styrene-butadiene copolymer, carboxylated styrene butadiene copolymer, acrylic ester copolymer, methacrylic ester copolymer, glass and kaolin;
   (2) reacting said immune complex with a second antibody or antigen also having a specific binding capacity for said target substance to form an immunoconjugate wherein said second antibody or antigen is coupled to a marker compound having a photothermal conversion activity selected from the group consisting of azo dyes, phenothiadione dyes, acridine dyes, phthalocyanine dyes, squaric acid dyes, colloid gold, iron-oxine complex and phycocyanin, with the proviso that said carrier substance amplifies the photothermal conversion activity of said marker compound when irradiated with an excitation beam having a specified wavelength;
   (3) irradiating the second reacted sample containing said immunoconjugate with said excitation beam having said specified wavelength; and
   (4) measuring the amount of heat generated by said coupled marker compound by measuring deflection of a probe beam passing through said irradiated sample by photothermal deflection spectroscopy to determine the amount of said target substance in said test sample.

2. The method according to claim 1, wherein the average particle diameter is in the range of 10 to 50 μm.

3. The method according to claim 1, wherein the amount of coupled marker compound in the test sample is determined by photothermal deflection spectroscopy without separating the immunoconjugate from the second reacted sample.

* * * * *

UNITED STATES PATENT AND TRADEMARK OFFICE
CERTIFICATE OF CORRECTION

PATENT NO. : 5,439,830

DATED : August 8, 1995

INVENTOR(S) : HAJIME SAKASHITA, ET AL.

It is certified that error appears in the above-indentified patent and that said Letters Patent is hereby corrected as shown below:

COLUMN 54

Title,"AT" should read --AN--.

COLUMN 75

Inventors, "Tsuguo Swada" should read --Tsuguo Sawada--.

COLUMN 1

Line 2, "at" should read --AN--;

Line 10, "it" should read --it is--;

Line 66, "immobilised" should read --immobilized--.

UNITED STATES PATENT AND TRADEMARK OFFICE
CERTIFICATE OF CORRECTION

PATENT NO. : 5,439,830
DATED : August 8, 1995
INVENTOR(S) : HAJIME SAKASHITA, ET AL.

It is certified that error appears in the above-indentified patent and that said Letters Patent is hereby corrected as shown below:

COLUMN 3

Line 4, "to" should be deleted.

COLUMN 4

Line 52, "e.g." should read --e.g.,--.

COLUMN 8

Line 32, "colloid" should read --colloidal--.

Signed and Sealed this

Twenty-fifth Day of June, 1996

BRUCE LEHMAN

Attesting Officer　　　　Commissioner of Patents and Trademarks